US011630292B2

(12) United States Patent
Schumann et al.

(10) Patent No.: US 11,630,292 B2
(45) Date of Patent: Apr. 18, 2023

(54) OPTICAL SCANNING MICROSCOPE AND EXAMINATION METHOD

(71) Applicant: Leica Microsystems CMS GmbH, Wetzlar (DE)

(72) Inventors: Christian Schumann, Lich (DE); Albrecht Weiss, Linden (DE); Tobias Bauer, Koenigstein (DE); Cornell Peter Gonschior, Friedberg (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 546 days.

(21) Appl. No.: 16/300,966

(22) PCT Filed: May 12, 2017

(86) PCT No.: PCT/EP2017/061470
§ 371 (c)(1),
(2) Date: Nov. 13, 2018

(87) PCT Pub. No.: WO2017/194742
PCT Pub. Date: Nov. 16, 2017

(65) Prior Publication Data
US 2020/0319445 A1 Oct. 8, 2020

(30) Foreign Application Priority Data

May 13, 2016 (DE) .................. 10 2016 108 987

(51) Int. Cl.
*G02B 21/00* (2006.01)
*G02B 21/06* (2006.01)
(Continued)

(52) U.S. Cl.
CPC ..... *G02B 21/0032* (2013.01); *G02B 21/0092* (2013.01); *G02B 21/02* (2013.01); *G02B 27/283* (2013.01); *G02B 21/0076* (2013.01)

(58) Field of Classification Search
CPC .. G02B 21/00; G02B 21/002; G02B 21/0028; G02B 21/0032; G02B 21/0068;
(Continued)

(56) References Cited

U.S. PATENT DOCUMENTS 6,091,523 A * 7/2000 Brandstetter ........ H04B 10/671
342/58
7,187,494 B2 3/2007 Nishiwaki et al.
(Continued)

FOREIGN PATENT DOCUMENTS

DE   102005020545 A1   11/2006
DE   102006033306 A1   1/2008
(Continued)

OTHER PUBLICATIONS

Eric A.J. Reits, et al., „From fixed to FRAP: measuring protein mobility and activity in living cells, Nature Cell Biology, vol. 3, Jun. 2001, pp. E145-E147.
(Continued)

*Primary Examiner* — Thong Q Nguyen
(74) *Attorney, Agent, or Firm* — Leydig, Volt & Mayer, Ltd.

(57) ABSTRACT

An optical scanning microscope includes an illumination system having a light source portion emanating from a light source, first and second polarizing beam splitters, and first and second optical channels disposed between the beam splitters. The light source portion is configured to emit a first illumination light beam comprising light of a first main polarization direction and of a second main polarization direction. The first beam splitter is configured to guide the light primarily into the first and channels, respectively. The second beam splitter is configured to form a second illumination light beam from light of the first and second main polarization directions from the first channel and second
(Continued)

channels, respectively. The first and second channels are configured to emit the light of the first and second main polarization directions from the first and second channels, respectively, so as to have different types of convergence.

17 Claims, 3 Drawing Sheets

(51) Int. Cl.
G02B 21/02 (2006.01)
G02B 27/28 (2006.01)

(58) Field of Classification Search
CPC .... G02B 21/0092; G02B 21/06; G02B 21/08; G02B 21/082; G02B 21/14; G02B 21/241
USPC .......................... 359/368–390, 483.1–494.1
See application file for complete search history.

(56) References Cited

U.S. PATENT DOCUMENTS

| 7,573,635 | B2 | 8/2009 | Uhl |
| 7,706,069 | B2* | 4/2010 | Mehl ................. G02B 27/281 |
| | | | 372/27 |
| 10,025,081 | B2 | 7/2018 | Euteneuer et al. |
| 10,095,017 | B2 | 10/2018 | Anhut et al. |
| 2003/0149425 | A1* | 8/2003 | Takada ................. A61F 9/008 |
| | | | 606/4 |
| 2006/0256426 | A1 | 11/2006 | Wolleschensky |
| 2007/0035821 | A1 | 2/2007 | Hecker |
| 2012/0176673 | A1* | 7/2012 | Cooper ................. G02B 27/283 |
| | | | 359/489.08 |
| 2013/0301096 | A1* | 11/2013 | Takahashi ............ G02B 26/105 |
| | | | 359/204.3 |
| 2014/0268330 | A1* | 9/2014 | Perkins .............. G02B 27/0994 |
| | | | 359/629 |
| 2015/0362714 | A1 | 12/2015 | Iga et al. |
| 2015/0377794 | A1* | 12/2015 | Nesbitt .............. G01N 21/8806 |
| | | | 356/369 |

FOREIGN PATENT DOCUMENTS

| DE | 102012010207 A1 | 11/2013 |
| DE | 102013222562 A1 | 5/2015 |
| EP | 1752809 B1 | 2/2007 |
| JP | 2011191496 A | 9/2011 |
| WO | WO 2011052248 A1 | 5/2011 |
| WO | WO 2013067643 A1 | 5/2013 |
| WO | WO 2016185170 A1 | 11/2016 |

OTHER PUBLICATIONS

Daniel Axelrod, "Total Internal Reflection Fluorescence Microscopy in Cell Biology", Munksgaard International Publishers; Traffic, vol. 2, Dec. 2001, pp. 764-774.

Jean M. Bennett, "Polarizers", Handbook of Optics, Fundamentals, Techniques & Design, vol. 2, Dec. 1995, pp. 3.1-3.70.

* cited by examiner

OPTICAL SCANNING MICROSCOPE AND EXAMINATION METHOD

CROSS-REFERENCE TO PRIOR APPLICATIONS

This application is a U.S. National Stage Application under 35 U.S.C. § 371 of International Application No. PCT/EP2017/061470 filed on May 12, 2017, and claims benefit to German Patent Application No. DE 10 2016 108 987.7 filed on May 13, 2016. The International Application was published in German on Nov. 16, 2017, as WO 2017/194742 A1 under PCT Article 21 (2).

The invention relates to an optical scanning microscope and to a corresponding examination method.

BACKGROUND

The examination of dynamic processes in biological systems is often of interest in modern functional biology. For this purpose, a possibility for spatial and temporal interaction with and/or manipulation of microscopic specimens is of particular importance. For this purpose, methods such as FRAP (fluorescence recovery after photobleaching), FLIP (fluorescence loss in photobleaching), uncaging and photoactivation are known. In methods of this kind, for the purpose of manipulation the specimen to be examined is typically scanned using a focused laser beam, a scanning apparatus (inserted in an orthoscopic beam path) being used.

At the same time, it is desirable to detect the progression of the experiment in a widefield microscope having the option of forming optical sections. A possibility for this is for example TIRF microscopy (total internal reflection fluorescence microscopy), in which a laser beam is focused into the entrance pupil of the objective in order to achieve planar illumination of the object field. Said illumination takes place at an adjustable angle which is determined by the position of the laser beam in the entrance pupil. Illumination at an angle that does not propagate through the boundary between the coverslip of the specimen and an aqueous specimen results in total reflection and slight illumination of the boundary by evanescent waves. In order to precisely set the illumination angle, a position control system for the laser beam in the entrance pupil is required. A scanning apparatus (inserted in a conoscopic beam path) can also be used for this purpose.

Regarding further details, reference is made to relevant specialist literature, for example, regarding TIRF microscopy reference is made to D. Axelrod, Traffic 2, 764-774 (2001), and regarding scan-based manipulation of microscopic specimens using scanning systems of confocal microscopes reference is made to E. A. J. Reits, Nat. Cell Biol. 3, E145-E147 (2001). Regarding the positioning of the laser beam in the entrance pupil, reference is made for example to DE 10 2006 033 306 A1.

In order to switch between the orthoscopic and conoscopic beam path, it is possible, for example according to U.S. Pat. No. 7,187,494 B2, to move a Bertrand lens assembly into the beam path of an orthoscopic scanning system in order to implement a conoscopic scanning system. However, this is disadvantageous in that the mechanical movement of the mirrors, prisms and lens systems is complex and in addition incompatible with the switching times, required in the statement of the problem, of less than the relevant biological timescales, e.g. of less than 10 ms.

U.S. Pat. No. 7,573,635 B2 describes switching using the scanning system itself. However, the method described requires a complex mirror system because the scanning mirror unit in the conoscopic beam path is used having a plurality of reflections, making a corresponding system complicated and laborious to handle.

EP 1 752 809 B2 discloses a system for combining orthoscopic and conoscopic illumination beam paths, but which has the disadvantage that still only a portion of the objective pupil is accessible for conoscopic illumination.

DE 10 2013 222 562 A1 describes an illumination means that can provide an orthoscopic and a conoscopic beam path. An annular mirror is used in this case. An illumination light beam that passes centrally through the annular mirror, i.e. through the unmirrored region thereof or a corresponding recess, is used for generating the orthoscopic beam path. An illumination light beam that impinges peripherally on the annular mirror, i.e. on the mirrored region thereof, is used for generating the conoscopic beam path. Therefore, here, only a portion of the beam path cross section can be used in each case for generating the orthoscopic beam path or conoscopic beam path.

SUMMARY

In an embodiment, the present invention provides an optical scanning microscope including an illumination system having a light source portion emanating from a light source, a first polarizing beam splitter and a second polarizing beam splitter, and a first optical channel and a second optical channel disposed between the first polarizing beam splitter and the second polarizing beam splitter. The light source portion is configured to emit a first illumination light beam comprising light of a first main polarization direction and of a second main polarization direction. The first polarizing beam splitter is configured to guide the light of the first main polarization direction at least primarily into the first optical channel, and to guide the light of the second main polarization direction at least primarily into the second optical channel. The second polarizing beam splitter is configured to form a second illumination light beam from light of the first main polarization direction from the first channel and from light of the second main polarization direction from the second channel. The first optical channel and second optical channel are configured to emit the light of the first main polarization direction from the first channel and the light of the second main polarization direction from the second channel so as to have different convergence angles.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

Mutually corresponding elements have been provided with identical reference signs in the figures. For the sake of clarity, repeated explanations will be omitted.

DETAILED DESCRIPTION

Figure 1:
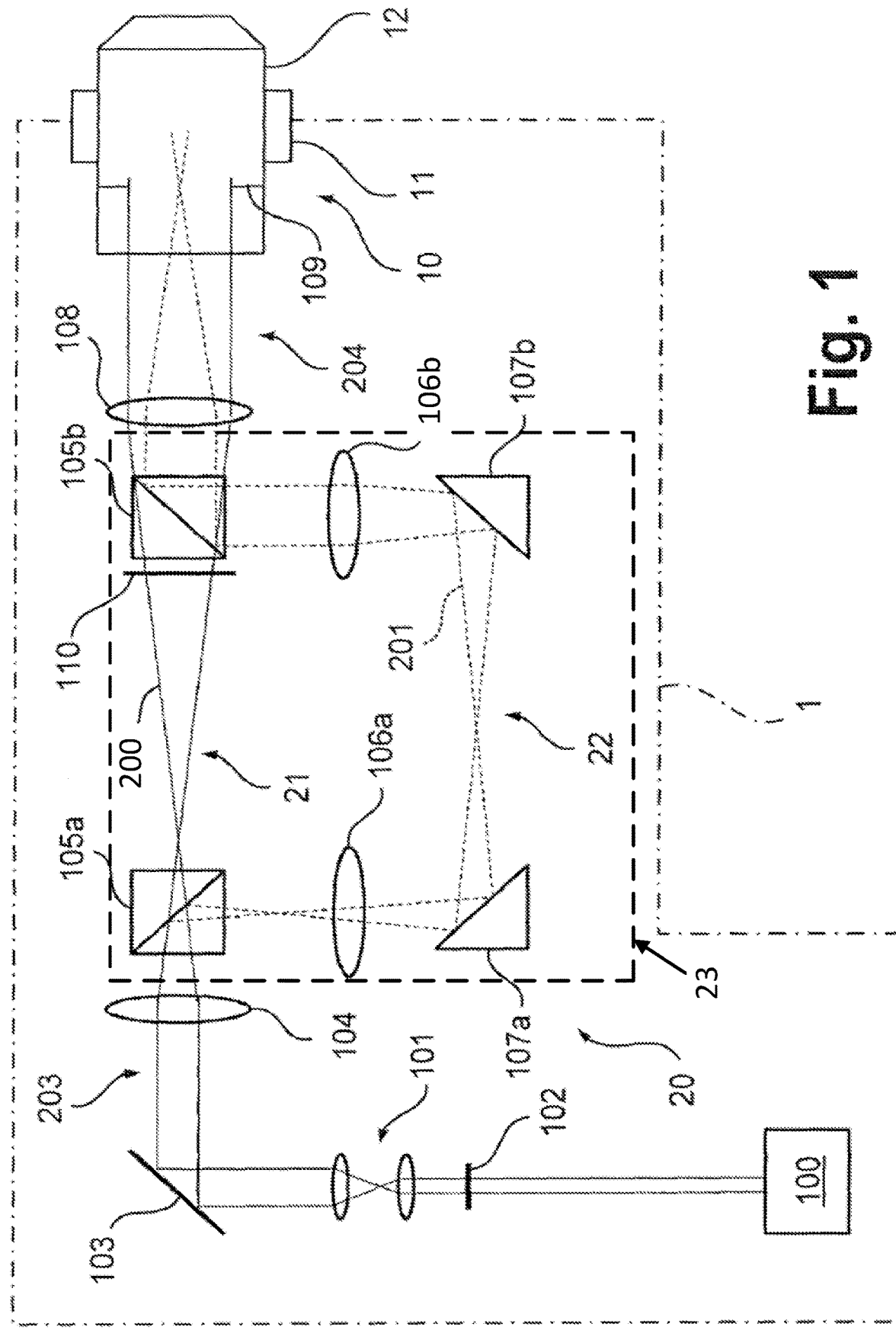
FIG. 1 is a simplified schematic view of a beam path of a scanning microscope comprising an illumination system according to an embodiment of the invention.

Embodiments of the present invention achieve control of a laser beam in the pupil, and scanning of a laser beam in the object field of a microscope using just one scanning unit. Furthermore, switching between the two uses of the scanning unit takes place quickly, with the result that, in the case of typical image acquisition rates of approximately 100 Hz, no interruptions occur in microscopic live-cell experiments.

The fundamental concept underlying embodiments of the present invention is that of keeping both an orthoscopic and a conoscopic beam path available in a scanning microscope at all times, and implementing switching between said two beam paths by means of polarized beam splitting. Combining the two beam paths is also achieved using polarization-optical means.

An embodiment of the present invention provides an optical scanning microscope that comprises an illumination system comprising a light source portion emanating from a light source, a first polarizing beam splitter and a second polarizing beam splitter, and a first optical channel and a second optical channel between the first beam splitter and the second beam splitter. A known scanning unit is integrated in the light source portion of the optical scanning microscope, as said unit is known in principle and will also be explained in more detail in the following.

When a "polarizing beam splitter" (PBS) is discussed here, this is to be understood as an optical element that refracts light of different polarization directions differently. For example, a polarizing beam splitter can allow light of a first polarization direction to pass through unrefracted, but in contrast, refract light of a second, different polarization direction by an angle defined by the construction and the optical materials. Regarding knowledge in the art with respect to polarizing beam splitters and the underlying physical basis, for the sake of simplicity reference is made to relevant technical literature, e.g. Bennett, J. M.: Polarizers, Chapter 3 in: Bass, M. E. et al. (eds.): Handbook of Optics. Fundamentals, Techniques & Design, Vol. 2, New York: McGraw-Hill, 2nd edition 1995.

In the case of the optical scanning microscope proposed, the light source portion is designed to emit a first illumination light beam comprising light of a first main polarization direction and a second main polarization direction.

In this case, within the meaning of the present invention, "light of a first main polarization direction" and "light of a second main polarization direction" are to be understood as light that primarily or exclusively comprises light waves that are in a first polarization direction and a second polarization direction, respectively, or of which the polarization directions are in each case in a narrow angular range of for example ±10°±5° or ±1°. It is possible that smaller portions may also be present in one or more further polarization directions, owing to incomplete polarization. In this case, the wording according to which corresponding light "primarily or exclusively" comprises light waves that are in the first polarization direction and in the second polarization direction, respectively, specifies, for example, that less than 25%, 10%, 5% or 1% is in a differing polarization direction. The first polarization direction and the second polarization direction are oriented so as to be mutually orthogonal. In this case, the orthogonal orientation includes both circularly polarized light and linearly polarized light that is present in two polarization directions.

In this case, according to the present invention the light of the first main polarization direction and of the second main polarization direction can be provided simultaneously, i.e. at one time, in the same illumination light beam. If this is the case, the illumination light beam comprises corresponding illumination light of a polarization state that corresponds to a linear combination of orthogonal main polarization directions. However, the illumination light beam can also be emitted in succession, having the first main polarization direction and then the second main polarization direction, as will also be explained in the following. In the latter case, the illumination light beam comprises light of primarily or exclusively of the first main polarization direction in a first time period, and light of primarily or exclusively of the second main polarization direction in a second time period. However, in this case too, the light does not necessarily have to be completely polarized; in order to cut out residual light of a differing polarization direction, it is possible to use for example an assembly, described below, comprising optical shutters.

The underlying inventive concept, specifically that of keeping the orthoscopic and the conoscopic beam path available simultaneously, is implemented by using the different optical channels between the first beam splitter and the second beam splitter. For this purpose, it is possible for the first beam splitter to be designed, in the scanning microscope according to an embodiment of the invention, to guide the light of the first illumination light beam that is of the first main polarization direction at least primarily into the first channel, and to guide the light of the first illumination light beam that is of the second main polarization direction at least primarily into the second channel. The light of the first main polarization direction and the light of the second main polarization direction are thus "treated" differently at the first beam splitter.

An illumination light beam that extends in a common beam path portion between the light source portion and the first beam splitter is thus transferred into the first channel or into the second channel, depending on the polarization. It is thus possible for the light of the first channel to be influenced differently from the light of the second channel, for example simply by means of different optical lengths of the two channels and/or by means of different optical elements in the two channels.

The light of the first main polarization direction or of the second main polarization direction which, according to the invention, is guided into the two channels is subsequently guided again into a common beam path portion. For this purpose, the second beam splitter is designed, according to the invention, to form a second illumination light beam from light of the first main polarization direction from the first channel and from light of the second main polarization direction from the second channel.

If, in this case, for example the light source portion emits the illumination light beam primarily or exclusively having light of the first main polarization direction in a first time period, said light primarily or exclusively enters the first channel and emerges therefrom into the second beam splitter. The second beam splitter then forms the second illumination light beam primarily or exclusively from the light from the first channel. The second illumination light beam thus primarily or exclusively comprises the light of the first main polarization direction. In a second time period, during which the light source portion emits the illumination light beam primarily or exclusively having light of the second main polarization direction, said light primarily or exclusively enters the second channel, via the first beam splitter, and emerges from said second channel and into the second beam splitter. The second beam splitter thus forms the second illumination light beam primarily or exclusively from the light of the second main polarization direction, from the second channel.

In contrast, if the light source portion emits the illumination light beam such that it comprises light of the first main polarization direction and of the second main polarization direction simultaneously, the light of the first main polarization direction primarily or exclusively enters the first channel, via the first beam splitter, and the light of the second main polarization direction passes primarily or exclusively into the second channel. In order to prevent both the light of the first main polarization direction and the light of the second main polarization direction from entering the beam splitter simultaneously from the first channel and the second channel, and the second illumination light beam thus being formed so as to be of the first main polarization direction and the second main polarization direction simultaneously, which may not be desirable, suitable optical shutters may be formed in the first channel and/or in the second channel in each case, which shutters in each case optically block either the first channel or the second channel. It is thereby possible to ensure that the second beam splitter always forms the second illumination light beam only from light of one of the two main polarization directions.

As already mentioned, according to the invention, the two optical channels mentioned are designed to emit the light of the first main polarization direction from the first channel and the light of the second main polarization direction from the second channel so as to have different convergence angles.

For example, the first channel may be designed to emit the light of the first main polarization direction in the form of a divergent light beam or light pencil, and the second channel may be designed to emit the light of the second main polarization direction from the second channel in the form of a collimated light beam. For this purpose, as already mentioned, different optical path lengths and/or optical elements are provided in the two channels. However, it is possible in principle to keep an orthoscopic and a conoscopic beam path available in parallel in manners other than that explained here and in the following.

In a corresponding scanning microscope, the light source portion is advantageously designed to provide the first illumination light beam in the form of a collimated light pencil, i.e. one light source is imaged into infinity. However, using the two different channels it is possible to subsequently either image a scanning unit along the orthoscopic beam path into the objective pupil and from there through a telecentric objective on the object side and into infinity, the light source being imaged in the specimen (front focal plane of the objective), or the scanning unit is imaged along the conoscopic beam path and into the specimen, the light source again remaining infinite.

Advantageously, a first optical element is arranged in front of the first beam splitter, which element is designed to shine the illumination light beam, provided in the form of the collimated light pencil, into the first beam splitter in the form of a convergent light pencil. Since, within the context of the present invention, said first beam splitter advantageously does not have any convergence-influencing properties, the light that is shone into the first beam splitter in the form of the convergent light pencil is also guided out of said first beam splitter and into the above-mentioned channels in a convergent manner. In the simplest case, the first optical element may for example be in the form of a converging lens, optionally comprising appropriate optical corrective means. Said element focusses the collimated light pencil of the illumination light beam into an image-side plane of the first optical element. In this way, the light that is focused using the first optical element diverges beyond the focal point of the first optical element and can thus for example be shone, in the form of a divergent light pencil, out of the first channel and into the second beam splitter, without any further optical influence. In the second optical channel, using suitable optical elements and deflection means, a corresponding light pencil that diverges beyond the focal point can be deflected, collimated, and shone, in a collimated manner, out of the second channel and into the second beam splitter. In particular, a portion of a Bertrand lens system, as known from DE 10 2013 222 562 A1, can be provided in the second channel for this purpose. The remainder of the Bertrand lens system is advantageously formed by a second optical element which is explained below and is located beyond the second beam splitter, for example a tube lens.

As already mentioned, the first channel is advantageously designed to shine light into the second beam splitter in an at least primarily divergent manner, and the second channel is advantageously designed to shine light into the second beam splitter in an at least primarily collimated manner. Since the first channel primarily or exclusively guides light of the first main polarization direction, said light is shone in the form of a divergent light pencil out of the first channel and into the second beam splitter. In contrast, the light of the second main polarization direction from the second channel is shone into the second beam splitter in the form of a collimated light pencil. Corresponding light can be optically influenced in any manner desired after passing through the second beam splitter.

Advantageously, a second optical element, already mentioned, is arranged in particular after the second beam splitter, which element is designed to collimate light (of primarily or exclusively the first main polarization direction) that is emitted divergently from the second beam splitter, and to focus light (of primarily or exclusively the second main polarization direction) that is emitted divergently from the second beam splitter. Said second optical element may in particular be the tube lens of the scanning microscope.

In particular, accordingly collimated light can be shone into an objective, it being possible for the angle at which said collimated light strikes a rear objective pupil to be changed using a scanning unit. Scanning illumination and specimen manipulation can be implemented in this manner. Focusing the collimated light pencil from the second beam splitter into the rear objective pupil makes it possible to achieve evanescent illumination for example, by means of the lateral focus position in the rear objective pupil being influenced by the scanning unit. This influences the angle of emergence of the light pencil that is in turn collimated by the objective, and thus the angle of incidence of the light pencil on the specimen or on the boundary between the immersion medium or coverslip and the specimen.

The present invention is therefore particularly advantageous in connection with an optical scanning microscope comprising an objective that has a rear objective pupil and can be mounted in an objective holder and positioned in an objective position, the second optical element being designed to focus the light of the second main polarization direction in a plane of the rear objective pupil. In contrast, the light of the first main polarization direction that is collimated by the second optical element passes through the rear objective pupil in collimated form.

As also already mentioned, the light source portion can provide light of the first main polarization direction and of the second main polarization direction simultaneously or can provide light of the first main polarization direction during a first time period and light of the second main polarization direction during a second time period. In the latter case, the light source portion used preferably switches rapidly between light of the first main polarization direction and light of the second main polarization direction.

A switchable retardation element is advantageously used to achieve correspondingly rapid switching between light of the first main polarization direction and light of the second main polarization direction. Said switchable retardation element may for example comprise a retardation plate, for example a λ/2 plate or a plurality of corresponding plates, that can be pivoted into the beam path of the light source portion or that is rotatably arranged in the beam path. However, electro-optical systems and/or acousto-optical systems and/or systems that are based on liquid crystals can also be used particularly advantageously as retardation elements. Corresponding elements for providing polarized light are known in principle from the prior art, and therefore reference can be made in this respect to relevant specialist literature.

In contrast, if, as is also possible in principle, the light source portion emits light of two different main polarization directions simultaneously, for example by means of light from two lasers of different polarizations being used and being combined in the first illumination light beam, or due to insufficient polarization of the light in one main polarization direction, e.g. due to inadequacies in the polarization-optical components, a fast shutter may also be provided in one or both of the channels, instead of a corresponding retardation element or even in addition thereto. In this case, whenever light of a first main polarization direction from the first channel is required, the second channel is blocked by a corresponding shutter, and vice versa. Correspondingly fast shutters may be designed for example in the form of synchronized rotating apertures or aperture segments, iris diaphragms, fast LCD apparatuses, electro-optical elements and/or acousto-optical elements.

In an optical scanning microscope according to a particularly preferred embodiment of the invention, optical elements are provided along the first channel, which elements are designed and arranged so as to form a Galilean telescope that images one or more real or virtual refraction points of the scanning means in or near the objective pupil. In this case, a "real or virtual refraction point" denotes a point that refracts light from a light source onto a corresponding scanning unit in a spatially restricted ("punctiform") manner and thus provides a scanning light beam. Corresponding refraction points are "real" when they are formed by elements that are actually present, for example mirrors; "virtual" refraction points are images of corresponding elements in space.

The illumination system according to the present invention is particularly advantageously designed to be removable, wherein in particular the first beam splitter and the second beam splitter and the first channel and the second channel, formed between the first beam splitter and the second beam splitter, are arranged on a slide (e.g., slide 23 shown in FIG. 1 and described below) that can be removed from the scanning microscope. The optical scanning microscope advantageously comprises means for adaptation to a widefield microscope, as a submodule.

The present invention also relates to a method for examining a specimen using an optical scanning microscope that comprises an illumination system comprising a light source portion, a first polarizing beam splitter and a second polarizing beam splitter, and a first optical channel and a second optical channel between the first beam splitter and the second beam splitter.

According to the method according to the invention, the light source portion is used to emit a first illumination light beam comprising light of a first main polarization direction and a second main polarization direction, the first beam splitter is used to guide the light of the first main polarization direction at least primarily into the first channel and the light of the second main polarization direction at least primarily into the second channel, the second beam splitter is used to form a second illumination light beam from light of the first main polarization direction from the first channel and light of the second main polarization direction from the second channel, and the first channel is used to emit the light of the first polarization and the second channel is used to emit the light of the second polarization so as to be at different convergence angles.

In particular a scanning microscope, as described and explained in detail above, can be used in a corresponding method. With regard to features and advantages of a corresponding method, reference is explicitly made to the explanations above.

Further advantages and embodiments of the invention can be found in the description and the accompanying drawings.

Of course, the features mentioned above and those explained below can be used not only in the combination specified in each case, but instead also in other combinations or alone, without departing from the scope of the present invention.

The invention is illustrated in the drawings on the basis of an embodiment, and will be described in the following with reference to the drawings.

Figure 2:
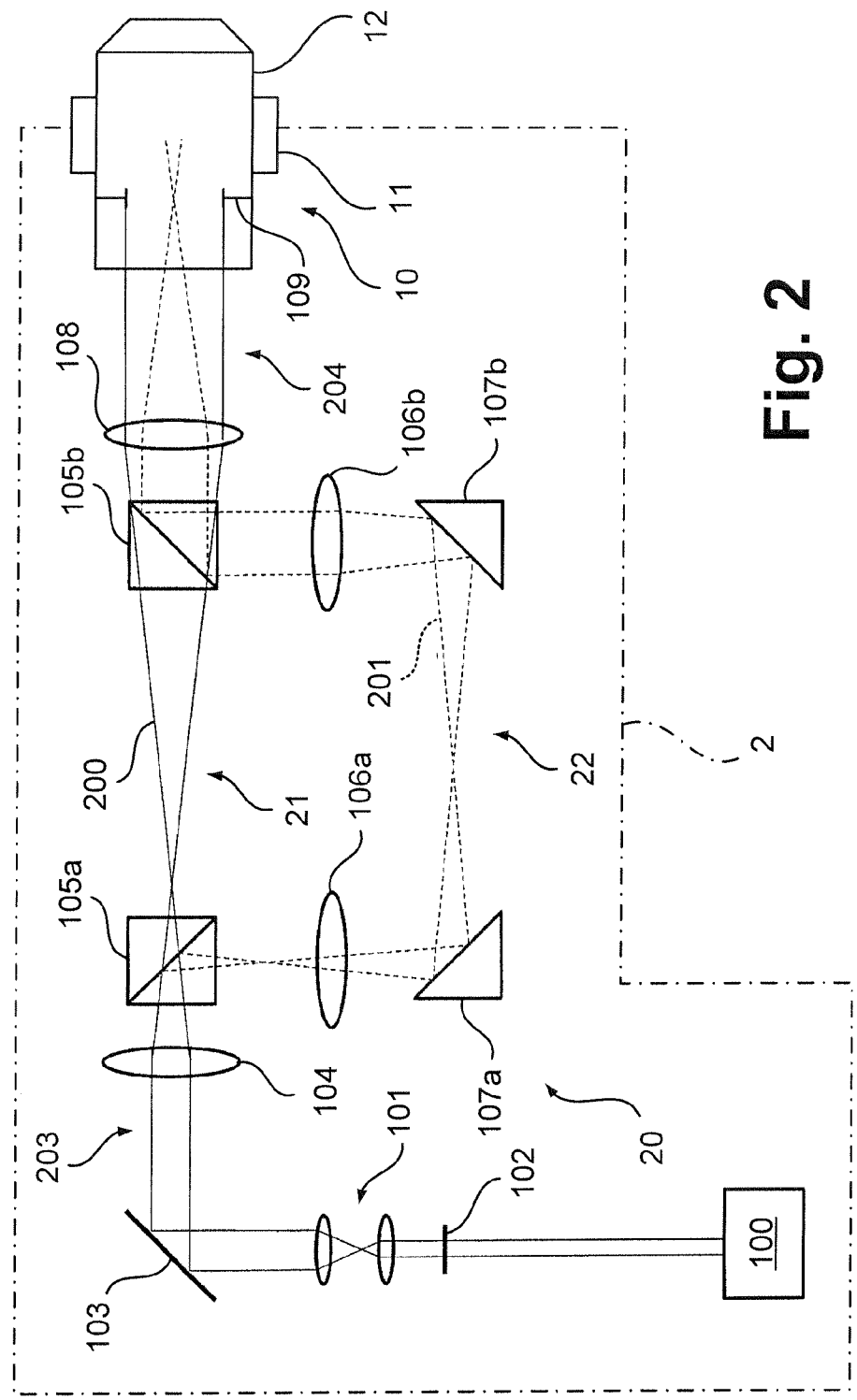
FIG. 2 is a simplified schematic view of a beam path of a scanning microscope comprising an illumination system without a shutter according to an embodiment of the invention.
Figure 3:
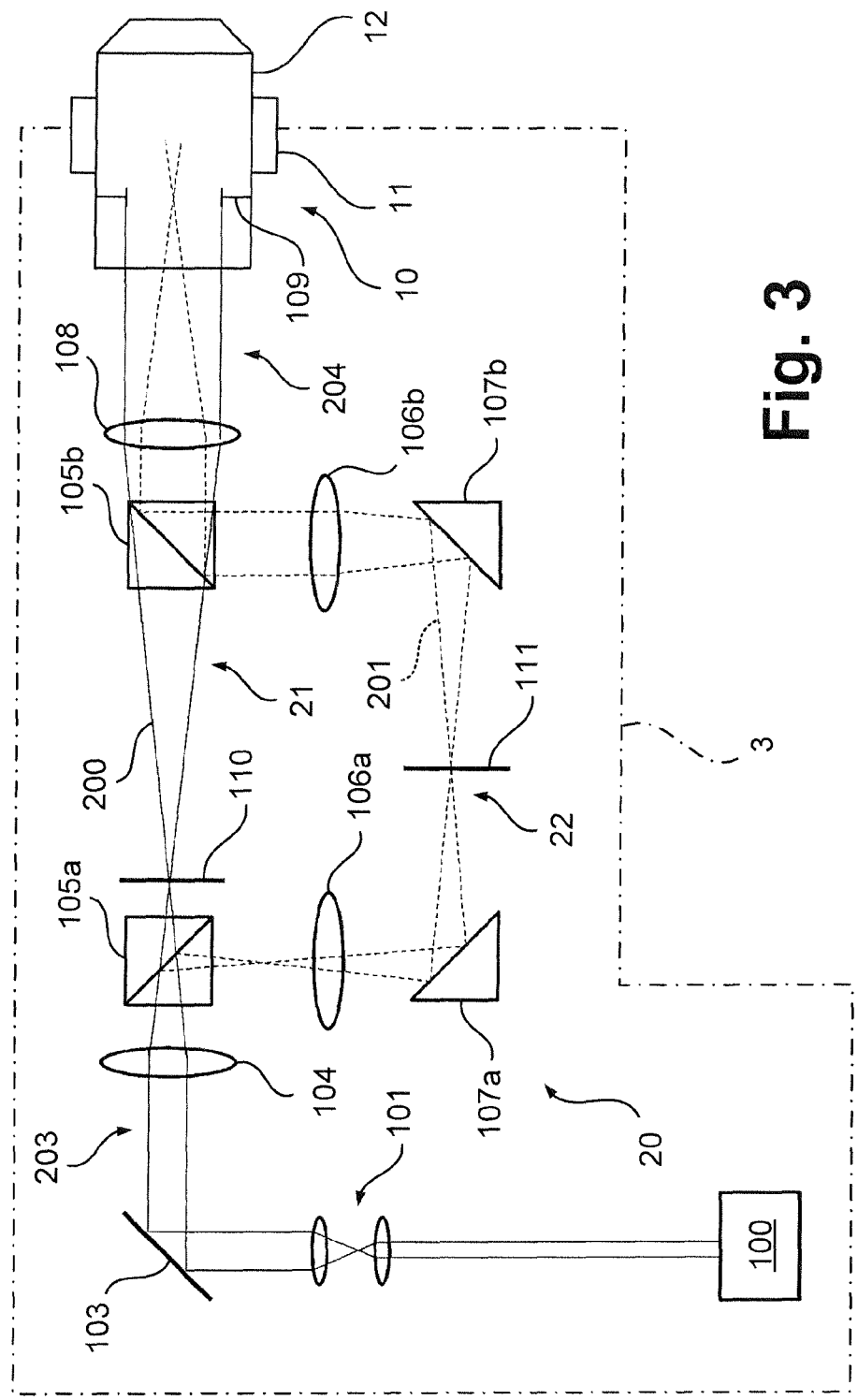
FIG. 3 is a simplified schematic view of a beam path of a scanning microscope comprising an illumination system without a variable retardation element according to an embodiment of the invention.

FIGS. 1 to 3 are in each case simplified schematic views of beam paths of a scanning microscope comprising an illumination system according to an embodiment of the invention. In this case, the embodiments shown in FIGS. 1 to 3 comprise a plurality of common elements which will first be explained in the following with reference to FIG. 1. The explanations also apply for the remaining figures.

A scanning microscope shown in FIG. 1, which microscope is shown here in dashed lines and in a highly schematic simplified manner overall and is denoted by 1, comprises an objective 12 that is received in an objective holder 11 and is in an objective position 10. Objective holders of various kinds may be provided, for example nosepieces, linear lens changers and the like. An objective pupil of the objective 12 is denoted by 109.

An illumination system of a corresponding scanning microscope is denoted as a whole by 20. An orthoscopic beam path is denoted by 200, and a conoscopic beam path is shown (dashed) by 201. In this case, the orthoscopic beam path 200 and the conoscopic beam path 201 extend together over specific stretches of the illumination system 20 or of a beam path formed therein, but extend in a first optical channel 21 and a second optical channel 22 so as to be mutually separate. In this case, the first channel 21 and the second channel 22 are each formed between a first polarizing beam splitter 105a and a second polarizing beam splitter 105b.

Two, for example mutually orthogonal, main polarization directions of an illumination light beam provided by a light source 100 are used for switching between the orthoscopic and the conoscopic beam path 201. A corresponding light source 100 that provides already correspondingly polarized illumination light can be used for this purpose. The light source 100 may for example be a laser light source, a polarization-maintaining optical fiber or a suitable polarization element, or a light source for unpolarized light comprising a corresponding polarization element.

Switching of the main polarization direction of an illumination light beam provided by a corresponding light source 100 can be achieved by various apparatuses, shown in a highly simplified manner here and denoted by a corresponding apparatus 102 (e.g., a retardation element). For example, the corresponding apparatus 102 may comprise a rapidly mechanically switchable retardation element (for example a 212 plate) that is preferably arranged at a point of the beam path or of the illumination light beam having a smaller beam diameter and a constant beam position. For example, the corresponding assembly 102 (e.g., the retardation element) may be arranged between a fiber collimator and in front of a beam expansion system as is indicated here in a simplified manner by 101.

Further possibilities for switching between the main polarization directions using the corresponding assembly 102 are for example acousto-optical, electro-optical or liquid crystal elements, as are known in principle from the prior art.

In the embodiment of the present invention shown in FIG. 1, a light source portion formed of the light source 100, the corresponding assembly 102, the beam expansion system 101 and a scan means 103 always provides light either of a first main polarization direction or of a second main polarization direction. Differing embodiments are explained for example with reference to FIG. 3.

A scan means or scanning unit 103 is designed in a manner known per se, for example comprising tiltable mirrors, rotatable prisms and/or acousto-optical means as are also known in principle from the prior art. Overall, the light source portion 100 to 103 thus provides an illumination light beam, denoted here by 203, which optionally has a first main polarization direction or a second main polarization direction and, in the example shown, is emitted from the scanning unit 103 in collimated form.

The illumination light beam 203 subsequently passes through a first optical element 104 consisting of one or more lenses and is thus focused. The illumination light beam 203 of the first main polarization direction or of the second main polarization direction enters the first polarizing beam splitter 105a in a focused or convergent manner. At a boundary layer of the first polarizing beam splitter 105a, the light of the second main polarization direction is reflected, as shown here in the form of the dashed conoscopic beam path 201, whereas light of the first main polarization direction passes unrefracted through the boundary layer.

In this way, the first polarizing beam splitter 105a guides the light of the first main polarization direction into the first optical channel 21 and the light of the second main polarization direction into the second channel 22. Beyond a corresponding focal point in the first channel 21 and in the second channel 22, respectively, the light of the first polarization and of the second polarization each extends divergently. In the example shown, the light of the first main polarization direction in the first channel 21, as shown here by the orthoscopic beam path 200, divergently emerges from the first channel and enters the second polarizing beam splitter 105b. In this case, a shutter 110 can prevent extraneous light from entering the second polarizing beam splitter.

In the embodiment shown in FIG. 1, no further optical elements are provided in the first channel 21. In contrast, further optical elements 106a and 106b are provided in the second optical channel 22. The light of the second polarization extending in the second channel 22 is furthermore deflected by deflection elements 107a and 107b. The optical elements 106a and 106b collimate the light of the second main polarization direction in the second channel 22, and said light enters the second polarizing beam splitter 105b in collimated form.

Correspondingly, the light of the first main polarization direction from the first channel 21 emerges divergently from the second polarizing beam splitter 105b after passing therethrough, whereas the light of the second main polarization direction from the second channel 22 emerges in a collimated manner from the second polarizing beam splitter 105b after passing through the second channel and through said second beam splitter. Using a second optical element 108, for example a tube lens, it is possible to focus the collimated light of the second main polarization direction from the second optical channel, but in contrast to collimate the light of the first main polarization direction from the first optical channel. The second optical element 108 forms, together with the above-described optical elements 106a and 106b, a Bertrand lens. The design of the first optical channel 21 and of the second optical channel 22, and the arrangement of the described lenses allow the light of the first main polarization direction to enter the rear objective pupil 109 of the objective 12 in collimated form, whereas the light of the second main polarization direction can be focused into the rear objective pupil 109 of the objective 12. The second optical element 108 forms, together with the first optical element 104, a Galilean telescope that images, in or close to the objective pupil 109, the real or virtual refraction point(s) of the illumination light beam brought about by the scan means 103.

Fluorescence light of a specimen that is arranged in front of the objective 12 can be detected using a conventional widefield fluorescence microscope. The illumination system 20 according to the embodiments described here can be coupled into and be removable from the fluorescence illumination beam path in a widefield fluorescence microscope of this kind, at a suitable point. For instance, in some embodiments, the slide 23, which is shown as the dotted line that surrounds the first and second optical channels 21 and 22 as well as the first and second polarizing beam splitters 105a and 105b, is removable from the scanning microscope 1. It is particularly advantageous for the Bertrand lens system formed by the optical elements 106a, 106b and 108 to comprise a variable focus that allows for focusing at different mechanical positions of the objective pupil 109, for example when using different objectives or a nosepiece focus. It is particularly advantageous for it to be possible for the second optical element 108, which, as mentioned, may be designed in the form of a tube lens for example, to be held constantly in a Bertrand lens system that can be focused accordingly, and therefore said element does not need to be removed even when the illumination system 20 is changed, provided that the afocality of the Galilean telescope, consisting of the elements 104 and 108, remains.

The embodiment of the scanning microscope 2 shown in FIG. 2 differs from the embodiment shown in FIG. 1 in that the shutter 110 is not present. As mentioned, in the embodiment of the scanning microscope 1 shown in FIG. 1, said shutter allows stray light owing to suboptimal light polarization to be cut out. If this is not required because adequately polarized light is already provided by a light source portion 100 to 103, said additional shutter 110 can be omitted, allowing for a simpler mechanical design of the microscope 2.

A corresponding assembly 102 (e.g., a variable retardation element), as is provided in the embodiments shown in FIGS. 1 and 2, is not provided in the embodiment of the scanning microscope 3 shown in FIG. 3. Instead, fast shutter elements 110 and 111 are provided both in the first channel 21 and in the second channel 22. In this case, the light source portion 100 to 103 or the light source 100 for example provides illumination light of a fixed polarization state that is a light linear combination of two orthogonal main polarization directions. Therefore, the first polarizing beam splitter 105a also directs illumination light into both channels 21 and 22. Alternate use of the shutters 110 and 111 of the two channels 21 and 22 then makes it possible to selectively block one beam path and to thereby guide light to the objective 12 through just one channel in each case. It is of course also possible to provide light through neither or through both of the channels 21 and 22, by corresponding control of the shutters 110 and 111.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE SIGNS 1, 2, 3 scanning microscope
10 objective position
11 objective holder
12 objective
20 illumination system
21 first optical channel
22 second optical channel
23 slide
100 light source
101 beam expansion system
102 corresponding apparatus
103 scanning unit
104 first optical element
105a, 105b polarizing beam splitters
106a, 106b further optical elements
107a, 107b beam deflection elements
108 second optical element
109 entrance pupil objective
110 shutter
111 shutter
200 orthoscopic beam path
201 conoscopic beam path
203 first illumination light beam
204 second illumination light beam

The invention claimed is:

1. An optical scanning microscope comprising:
an illumination system having a light source portion emanating from a light source, a first polarizing beam splitter and a second polarizing beam splitter, and a first optical channel and a second optical channel disposed between the first polarizing beam splitter and the second polarizing beam splitter, wherein:
the light source portion is configured to emit a first illumination light beam comprising light of a first main polarization direction and of a second main polarization direction,
the first polarizing beam splitter is configured to guide the light of the first main polarization direction at least primarily into the first optical channel, and to guide the light of the second main polarization direction at least primarily into the second optical channel,
the second polarizing beam splitter is configured to form a second illumination light beam from light of the first main polarization direction from the first channel and from light of the second main polarization direction from the second channel, and
the first optical channel and second optical channel are configured to emit the light of the first main polarization direction from the first channel and the light of the second main polarization direction from the second channel so as to have different convergence angles by emitting the light from the first channel in the form of a divergent light beam and emitting the light from the second channel in the form of a collimated light beam.

2. The optical scanning microscope according to claim 1, wherein the light source portion is configured to emit the first illumination light beam in a collimated manner.

3. The optical scanning microscope according to claim 2, wherein a first optical element is arranged in front of the first polarizing beam splitter, and wherein the first optical element is configured to focus the first illumination light beam and to shine the first illumination beam into the first polarizing beam splitter in a convergent manner.

4. The optical scanning microscope according to claim 3, wherein the first optical channel is configured to shine light into the second polarizing beam splitter in an at least primarily divergent manner, and wherein the second optical channel is configured to shine light into the second polarizing beam splitter in an at least primarily collimated manner.

5. The optical scanning microscope according to claim 4, wherein a second optical element is arranged after the second polarizing beam splitter, and wherein the second optical element is configured to collimate the light that is emitted divergently from the second polarizing beam splitter, and to focus light that is emitted in a collimated manner from the second polarizing beam splitter.

6. The optical scanning microscope according to claim 5, further comprising an objective that has a rear objective pupil and is mountable in an objective holder and positionable in an objective position, wherein the second optical element is configured to focus the light that emerges in a collimated manner from the second polarizing beam splitter in a plane of the rear objective pupil.

7. The optical scanning microscope according to claim 1, wherein at least a portion of a Bertrand lens system is disposed in the second channel.

8. The optical scanning microscope according to claim 1, wherein the first polarizing beam splitter and the second polarizing beam splitter cause the light of the first main polarization direction to travel through the illumination system in an orthoscopic beam path, and wherein the first polarizing beam splitter and the second polarizing beam splitter cause the light of the second main polarization direction to travel through the illumination system in a conoscopic beam path.

9. The optical scanning microscope according to claim 1, wherein the light source portion is configured to emit the first illumination light beam having the light of the first main polarization direction in a first time period and having the light of the second main polarization direction in a second time period.

10. The optical scanning microscope according to claim 9, further comprising a switchable retardation element configured to emit the first illumination light beam having the light of the first main polarization direction in the first time period and having the light of the second main polarization direction in the second time period.

11. The optical scanning microscope according to claim 1, wherein the light source portion is configured to emit the first illumination light beam having the light of the first main polarization direction and of the second main polarization direction simultaneously.

12. The optical scanning microscope according to claim 1, wherein the illumination system comprises a scanning unit.

13. The optical scanning microscope according to claim 1, wherein a first optical element is disposed between the light source portion and the first polarizing beam splitter and a second optical element is disposed between the second polarizing beam splitter and an objective pupil, and wherein the first optical element and the second optical element are designed and arranged so as to form a Galilean telescope that images one or more real or virtual refraction points of a scanning unit of the light source portion in or near the objective pupil.

14. The optical scanning microscope according to claim 1, wherein an optical shutter is arranged in the first optical channel or in the second optical channel.

15. The optical scanning microscope according to claim 1, wherein the first and the second polarizing beam splitters and the first and the second optical channels are arranged on a slide that is removable from the scanning microscope.

16. The optical scanning microscope according to claim 1, further comprising further comprising a submodule configured to adapt to a widefield microscope.

17. A method for examining a specimen using an optical scanning microscope comprising an illumination system having a light source portion, a first polarizing beam splitter and a second polarizing beam splitter, and a first optical channel and a second optical channel between the first polarizing beam splitter and the second polarizing beam splitter, the method comprising the steps of:

emitting a first illumination light beam comprising light of a first main polarization direction and of a second main polarization direction using the light source portion, guiding the light of the first main polarization direction at least primarily into the first optical channel, and guiding the light of the second main polarization direction at least primarily into the second channel, using the first polarizing beam splitter, forming a second illumination light beam from light of the first main polarization direction from the first channel and from light of the second main polarization direction from the second channel, using the second polarizing beam splitter, and using the first channel to emit the light of the first main polarization direction and using the second channel to emit the light of the second main polarization direction so as to have different convergence angles by emitting the light from the first channel in the form of a divergent light beam and emitting the light from the second channel in the form of a collimated light beam.

* * * * *